US010206559B2

(12) United States Patent
Sato et al.

(10) Patent No.: US 10,206,559 B2
(45) Date of Patent: Feb. 19, 2019

(54) ENDOSCOPE APPARATUS

(71) Applicant: OLYMPUS CORPORATION, Hachioji-shi, Tokyo (JP)

(72) Inventors: Eijiro Sato, Hachioji (JP); Kenji Takatsuji, Tokyo (JP); Chikayoshi Meguro, Hachioji (JP)

(73) Assignee: OLYMPUS CORPORATION, Hachioji-shi (JP)

( * ) Notice: Subject to any disclaimer, the term of this patent is extended or adjusted under 35 U.S.C. 154(b) by 94 days.

(21) Appl. No.: 15/377,305

(22) Filed: Dec. 13, 2016

(65) Prior Publication Data

US 2017/0086651 A1  Mar. 30, 2017

Related U.S. Application Data

(63) Continuation of application No. PCT/JP2015/067082, filed on Jun. 12, 2015.

(30) Foreign Application Priority Data

Jun. 20, 2014  (JP) .................................. 2014-127728

(51) Int. Cl.
*A61B 1/005* (2006.01)
*A61B 1/00* (2006.01)
*G02B 23/24* (2006.01)
*A61B 1/307* (2006.01)
*A61B 1/12* (2006.01)
*A61B 1/06* (2006.01)
*A61B 1/018* (2006.01)
*A61B 1/045* (2006.01)

(52) U.S. Cl.
CPC ........ *A61B 1/0052* (2013.01); *A61B 1/00066* (2013.01); *A61B 1/00114* (2013.01);
(Continued)

(58) Field of Classification Search
CPC ... A61B 1/0051; A61B 1/0052; A61B 1/0055; A61B 1/0057; A61B 1/008; A61B 1/018;
(Continued)

(56) References Cited

U.S. PATENT DOCUMENTS 5,922,018 A * 7/1999 Sarvazyan ........... A61B 1/0052
600/587
2010/0121147 A1* 5/2010 Oskin .................. A61B 1/0051
600/118

(Continued)

FOREIGN PATENT DOCUMENTS

EP   1 481 628 A1   12/2004
JP   H01-270843 A   10/1989
(Continued)

OTHER PUBLICATIONS

Feb. 14, 2018 Extended European Search Report issued in European Patent Application No. 15810175.8.
(Continued)

*Primary Examiner* — Timothy J Neal
*Assistant Examiner* — Aaron B Fairchild
(74) *Attorney, Agent, or Firm* — Oliff PLC

(57) ABSTRACT

The endoscope of the present embodiment is so configured that the forceps port connected to the insertion section can be rotated by connecting, like "L", the front section from which the insertion section extends and the rear housing section from which the cable extends, and the curving operation lever is placed at a middle position of the L-shaped connection. Thus, the front section serving as the first grasping section and the rear housing section serving as the second grasping section can be shifted to each other as a section to be grasped, and the positions of the curving operation lever and the forceps port and the positions of the fingers match irrespective of the grasping mode, with the result that the operation can be performed comfortably.

7 Claims, 13 Drawing Sheets

(52) U.S. Cl.
CPC .............. *A61B 1/018* (2013.01); *A61B 1/045* (2013.01); *A61B 1/0661* (2013.01); *A61B 1/12* (2013.01); *A61B 1/307* (2013.01); *G02B 23/2476* (2013.01)

(58) Field of Classification Search
CPC ......... A61B 1/045; A61B 1/0661; A61B 1/12; A61B 1/307; A61B 1/00066
USPC .................................................. 600/131, 137
See application file for complete search history.

(56) References Cited

U.S. PATENT DOCUMENTS

| | | |
|---|---|---|
| 2010/0160729 A1 | 6/2010 | Smith et al. |
| 2012/0165605 A1 | 6/2012 | Yamazaki |

FOREIGN PATENT DOCUMENTS

| | | |
|---|---|---|
| JP | 2006-110053 A | 4/2006 |
| JP | 2009-189684 A | 8/2009 |
| JP | 2009-189685 A | 8/2009 |
| WO | 2012/017810 A1 | 2/2012 |

OTHER PUBLICATIONS

Dec. 20, 2016 International Preliminary Report of Patentability issued in International Application No. PCT/JP2015/067082.

Sep. 8, 2015 International Search Report issued in Patent Application No. PCT/JP2015/067082.

May 31, 2016 Office Action issued in Japanese Patent Application No. 2016-507934.

* cited by examiner

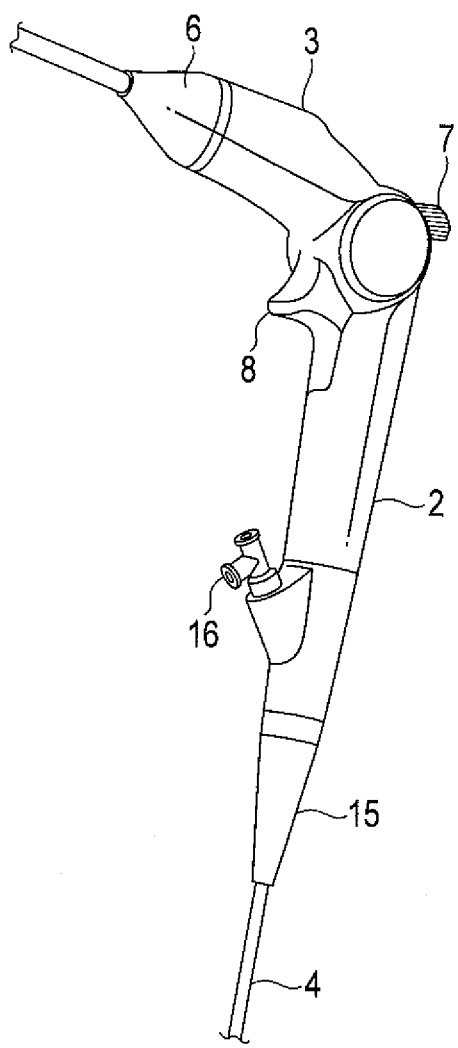
F I G. 5

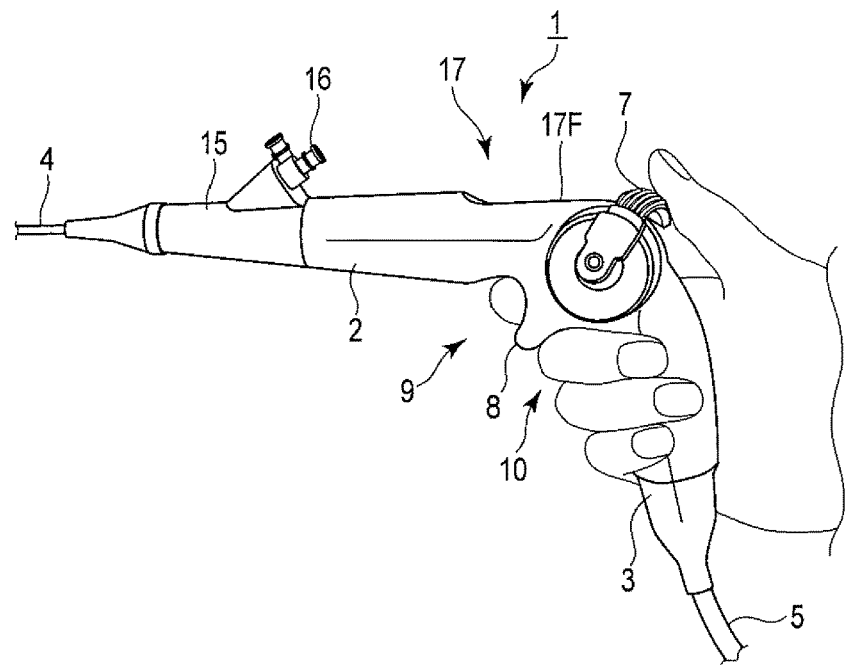
F I G. 6A
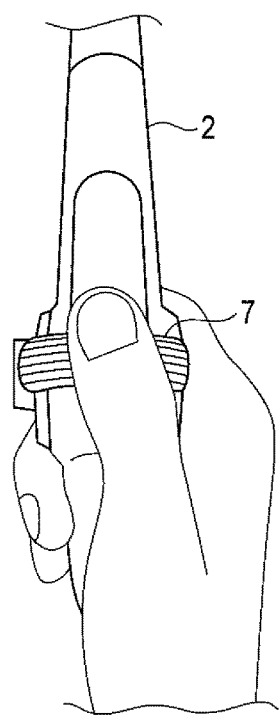
F I G. 6B

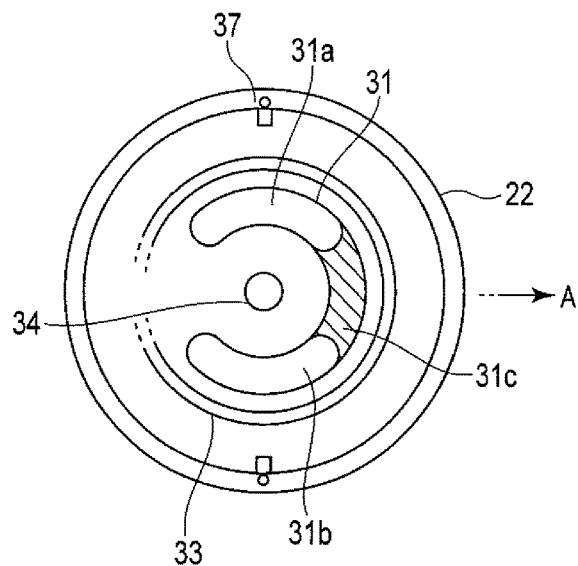
F I G. 10A
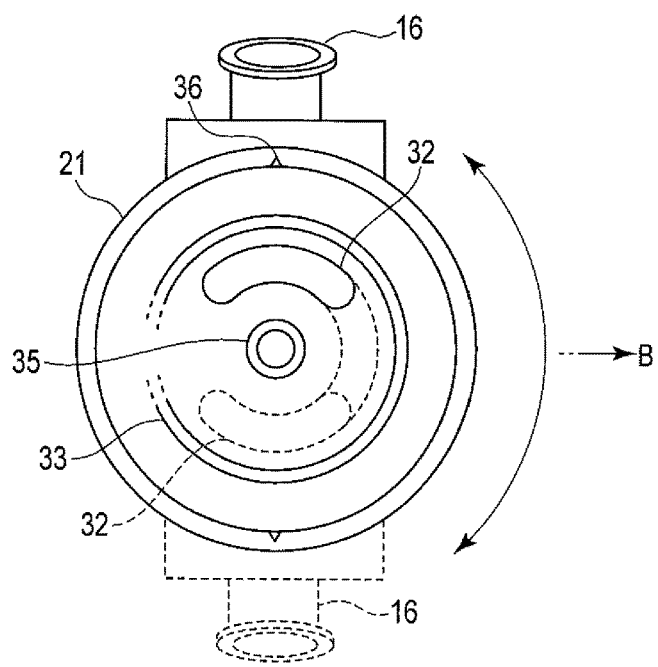
F I G. 10B

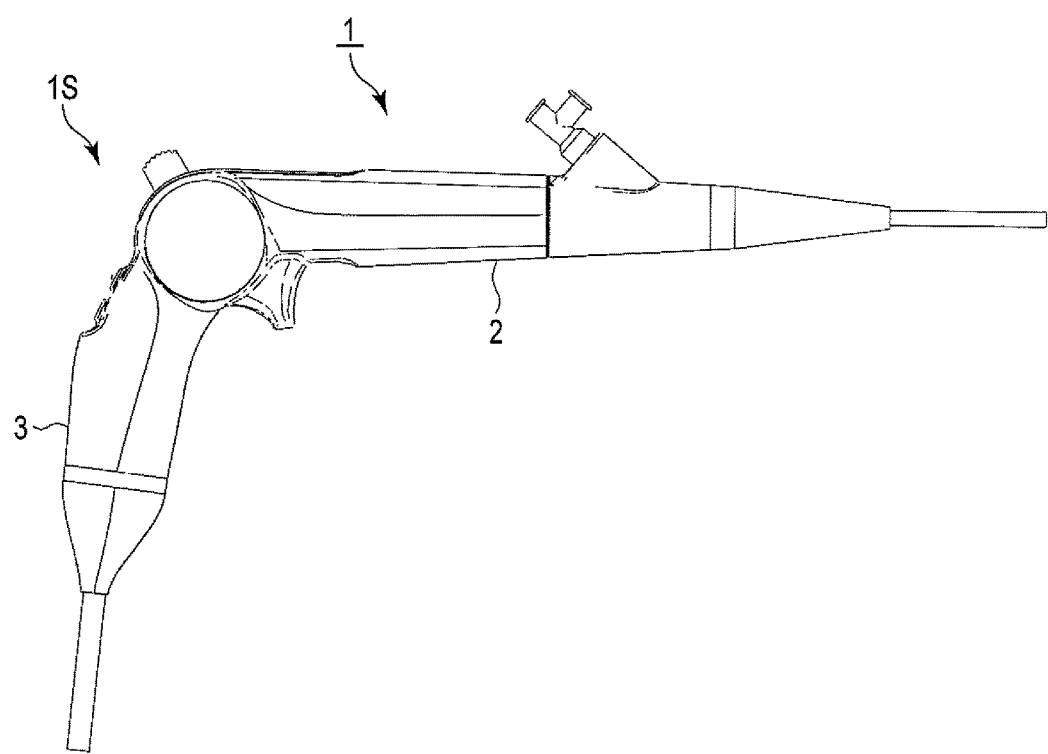
F I G. 12A

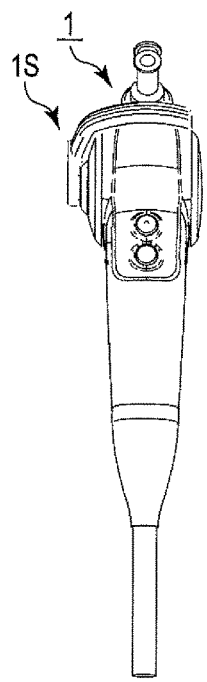
F I G. 12B
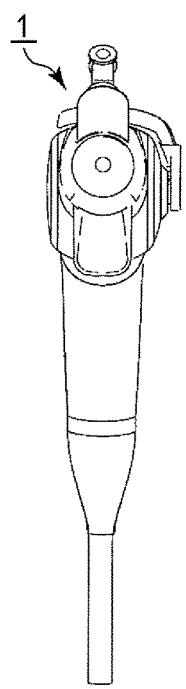
F I G. 12C

ENDOSCOPE APPARATUS

CROSS-REFERENCE TO RELATED APPLICATIONS

This is a Continuation application of PCT Application No. PCT/JP 2015/067082, filed Jun. 12, 2015, which was published under PCT Article 21(2) in Japanese. This application is based upon and claims the benefit of priority from prior Japanese Patent Application No. 2014-127728, filed Jun. 20, 2014 the entire contents of which are incorporated herein by references.

BACKGROUND OF THE INVENTION

1. Field of the Invention

The present invention relates to an endoscope apparatus including an operation unit operable in a plurality of grasping modes.

2. Description of the Related Art

In general, the operation unit (endoscope body) of an endoscope apparatus is grasped by one hand of an operator, and forceps are operated by the other hand. This operation unit is usually grasped and held by, for example, the left hand, and a curving operation lever to perform a curving operation of the insertion section and switches to supply and suck water are arranged at positions where each finger of the left hand reaches. Usually, an operator bends the left arm to raise the operation unit from the chest to the shoulders, and supports the halfway portion of an elongated insertion section extending downward from the operation unit by the right hand to change the insertion section toward the horizontal direction and insert it into an insertion opening located horizontally.

As for the ordinary operation unit, Jpn. Pat. Appln. KOKAI Publication No. 2009-189685 (patent literature 1) proposes a gun-shaped (L-shaped) operation unit whose insertion section extends in the horizontal direction. This operation unit has a grip portion to be gripped, and the insertion section extends in the horizontal direction from the front.

The operation unit has a proximal end at its lower portion and the insertion section extends downward. Because of this structure, it is difficult for an operator to perform an insertion operation unless the operator stands up to raise the operation unit to a level higher than the chest.

In contrast, the gun-shaped (L-shaped) operation unit of Jpn. Pat. Appln. KOKAI Publication No. 2009-189685 (patent literature 1) includes a grasping section and a front section that overhangs toward the front from an upper portion of the grasping section. The front section is provided with a proximal end of the insertion section, and the insertion section extends in the horizontal direction. With this structure, an operator can perform an inserting operation without standing up. On the other hand, in the conventional operation unit, when an operator tries to insert the insertion section in the horizontal direction, the operator has to take an uncomfortable posture such as that he or she rotates his or her wrist and raises the operation unit on his or her shoulder. The conventional operation unit is not favorable in terms of operability.

The conventional operation unit has a curving mechanism in which a curving portion extends only in the up and down direction. When an operator makes an observation in the right and left direction, he or she has to rotate the operation unit, e.g. 90° around the axis of the insertion section to change a direction in which the insertion section is curved. The insertion section extends downward from the operation unit and is always used in the curved state. Thus, even though the operation unit is rotated 90°, the rotation is attenuated due to a deformation and the distal end of the insertion section is not always rotated 90°. In actuality, therefore, an operator sometimes rotates, more than necessary, the wrist of a hand with which the operator grasps the operation unit. If, furthermore, the insertion section is bent, it is assumed that the intrinsic torque follow-up and curving performance of the insertion section cannot be improved sufficiently due to a loss of the driving force transmission mechanism (e.g. wire and a pully) in the insertion section.

An embodiment of the present invention provides an endoscope including an operation unit which can be grasped in a plurality of modes as desired by an operator and which can be operated comfortably irrespective of an operator's grasping posture.

BRIEF SUMMARY OF THE INVENTION

According to an embodiment of the present invention, there is provided an endoscope comprising: an elongated insertion section including a curving portion, which is allowed to curve in a uniaxial direction, at a distal end and extending along a first longitudinal axis orthogonal to the uniaxial direction; a distal-end rotation section to which a proximal end of the insertion section is fixed and which has an opening into which an operating instrument is inserted; a first grasping section one end of which is connected to the distal-end rotation section such that the distal-end rotation section is allowed to rotate within an arbitrary angle range; a second grasping section connected L-shaped to the other end of the first grasping section, the second grasping section extending along a second longitudinal axis that forms a predetermined obtuse angle with the first longitudinal axis; a curving operation lever provided at the other end of the first grasping section and rotated at an initial position corresponding to half of a major angle which the first longitudinal axis and the second longitudinal axis form, to curve the curving portion; and a universal cable extending from a bottom end of the second grasping section toward a direction that is substantially parallel to the second longitudinal axis, the endoscope has a first mode in which an unconnected side of the first grasping section is a reference placement position in which the opening is placed and a second mode in which the distal-end rotation section rotates and the opening is placed on a connected side of the first grasping section which is opposed to the reference placement position, and the endoscope has a first grasping mode in which in the first mode, the second grasping section is grasped and the insertion section is extended in a horizontal direction that is substantially the same as a direction in which the insertion section is inserted into a subject and a second grasping mode in which in the second mode, the first grasping section is grasped and the insertion section is extended downward.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWINGS

The accompanying drawings, which are incorporated in and constitute a part of the specification, illustrate embodiments of the invention, and together with the general description given above and the detailed description of the embodiments given below, serve to explain the principles of the invention.

FIG. 5 is a diagram showing an outward appearance of the operation unit according to the embodiment grasped in a conventional grasping mode, which is viewed obliquely from the front.

FIG. 6A is a diagram showing a first example of the operation unit grasped in a first grasping mode, which viewed from one side thereof.

FIG. 6B is a diagram showing the first example of the operation unit grasped in the first grasping mode, which viewed from the top thereof.

FIG. 10A is a diagram showing an example of the structure of contact surface A of a front body shown in FIG. 2.

FIG. 10B is a diagram showing an example of the structure of contact surface B of a distal-end rotation section shown in FIG. 2.

FIG. 12A is a rear view of the outward appearance of the endoscope according to the embodiment.

FIG. 12B is a left-side view of the outward appearance of the endoscope according to the embodiment.

FIG. 12C is a right-side view of the outward appearance of the endoscope according to the embodiment.

DETAILED DESCRIPTION OF THE PREFERRED EMBODIMENT

An embodiment of the present invention will be described in detail below with reference to the drawings.

Figure 1:
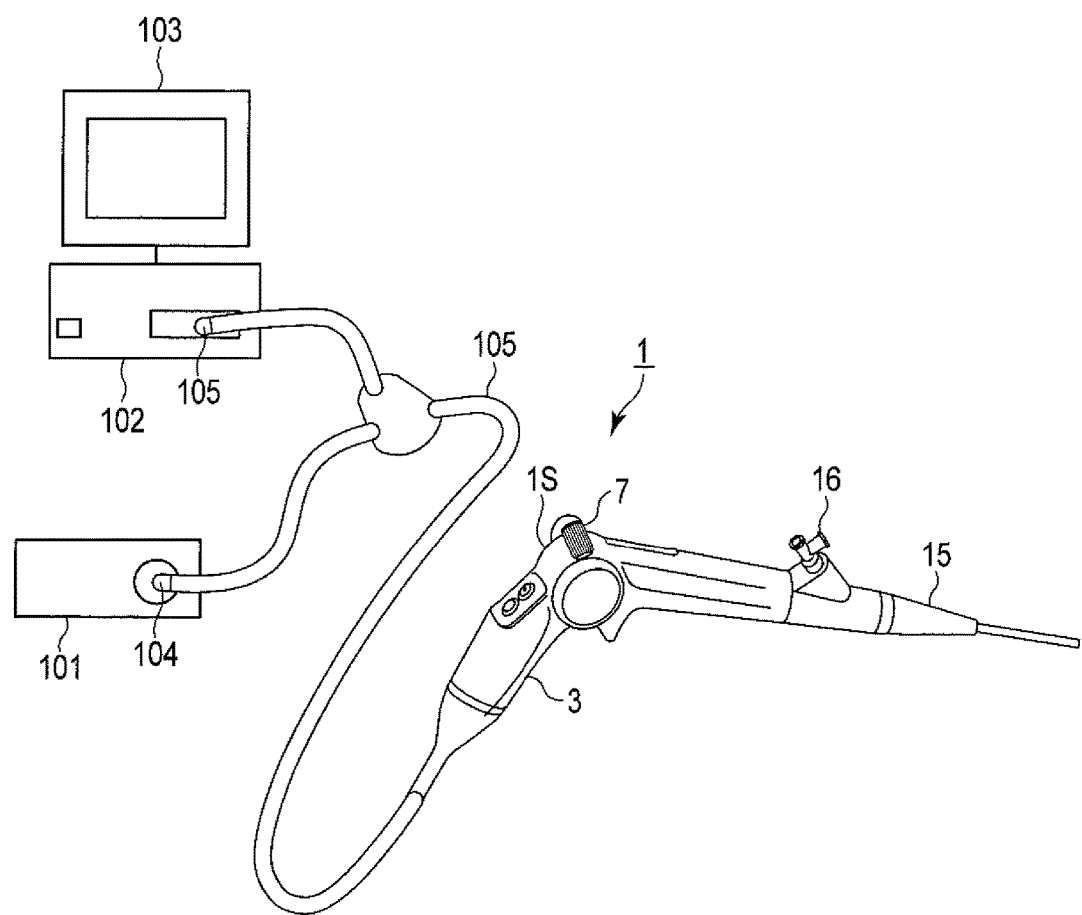
FIG. 1 is a diagram schematically showing an example of the whole structure of an endoscope apparatus according to one embodiment of the present invention, which is applied to an endoscope system for use in the field of urology.

FIG. 1 is a diagram schematically showing an example of the whole structure of an endoscope apparatus according to one embodiment of the present invention, which is applied to an endoscope system for use in the field of urology.

The endoscope apparatus includes an endoscope body 1, a light source device 101 which supplies illumination light, a video processor 102 including a camera control unit (CCU), which performs image processing for video signals picked up by an endoscope, and a monitor 103 which displays video signals output from the video processor 106. For example, a connector terminal 104 of the light source device 101 and a connector terminal 109 of the video processor 105 are connected to the endoscope body 1 through a universal cable 5. Though not shown, the endoscope apparatus may also include, for example, an image recording device that records video signals and a printer that prints images on paper and the like, which are connected to the video processor 102.

Figure 2:
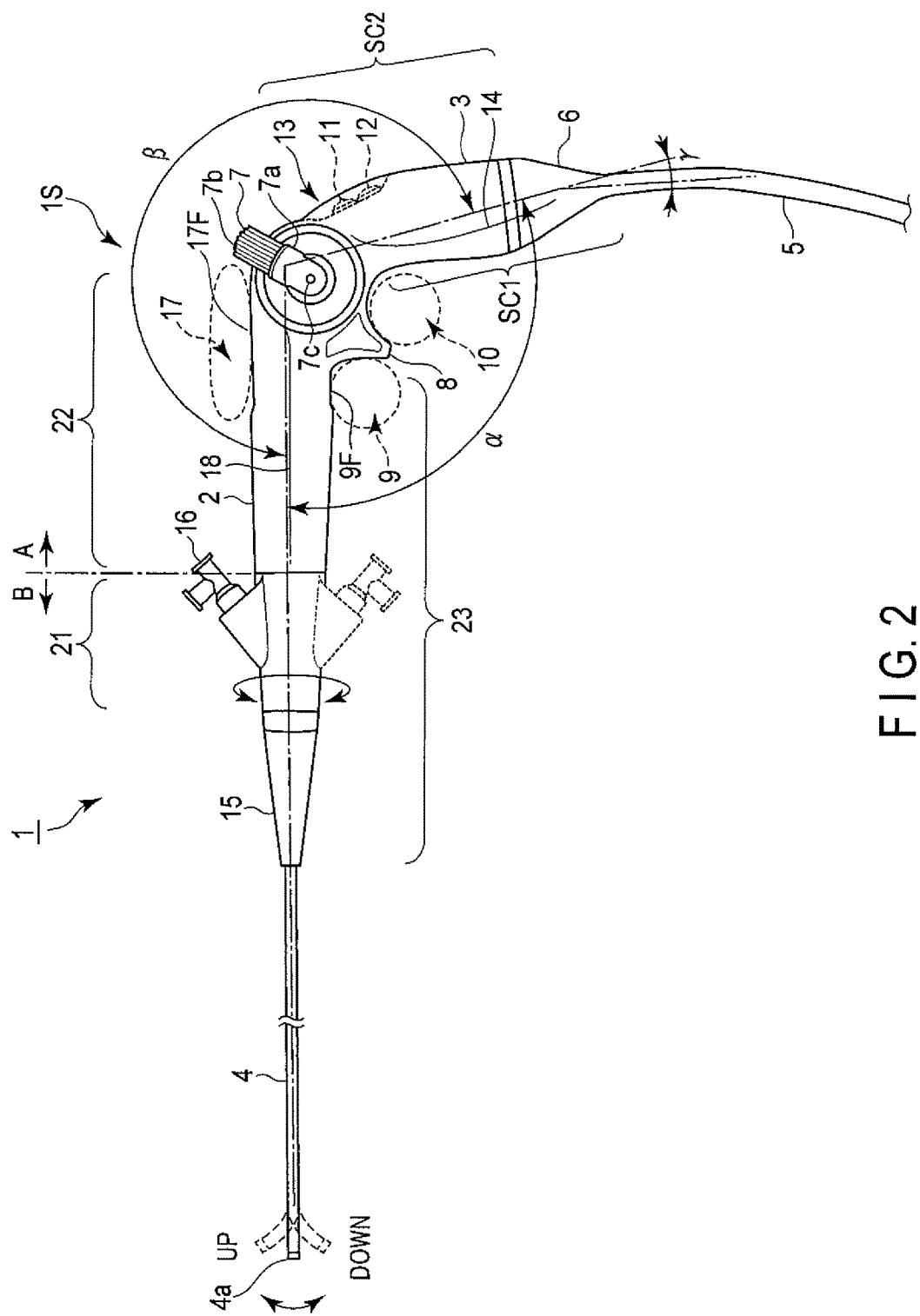
FIG. 2 is a diagram showing an outward appearance of an operation unit of the endoscope apparatus according to the embodiment of the present invention.
Figure 3A:
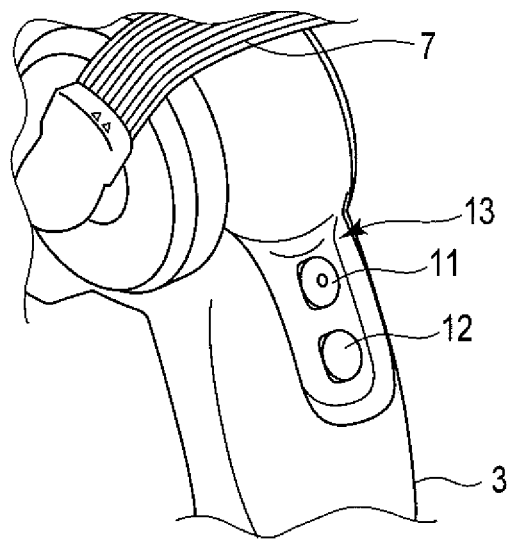
FIG. 3A is a diagram showing a first structure example of a switch provided in the upper part of a rear housing section of the operation unit.
Figure 4A:
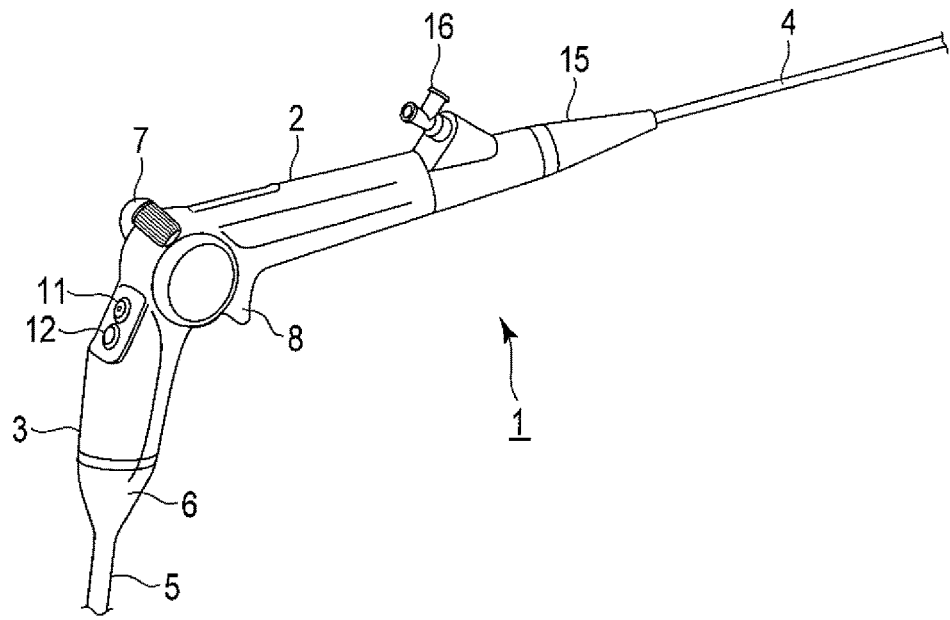
FIG. 4A is a diagram showing an outward appearance of the operation unit according to the embodiment, which is viewed obliquely from behind.
Figure 4B:
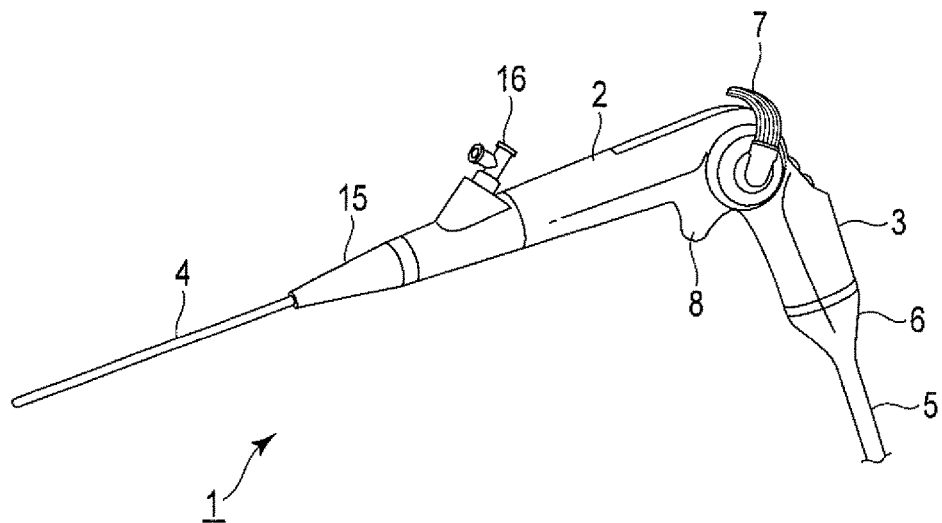
FIG. 4B is a diagram showing an outward appearance of the operation unit, which is viewed obliquely from the front.
Figure 11A:
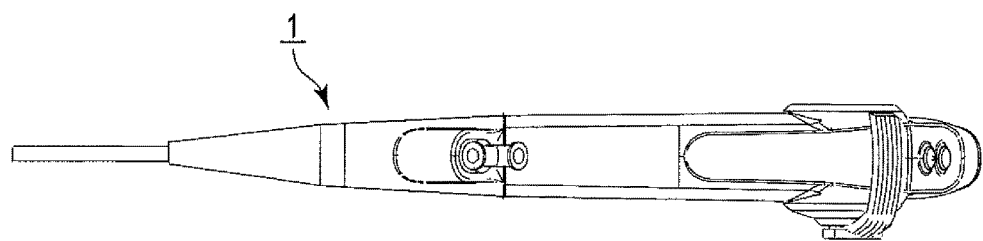
FIG. 11A is a plan view of an outward appearance of the endoscope according to the embodiment.
Figure 11B:
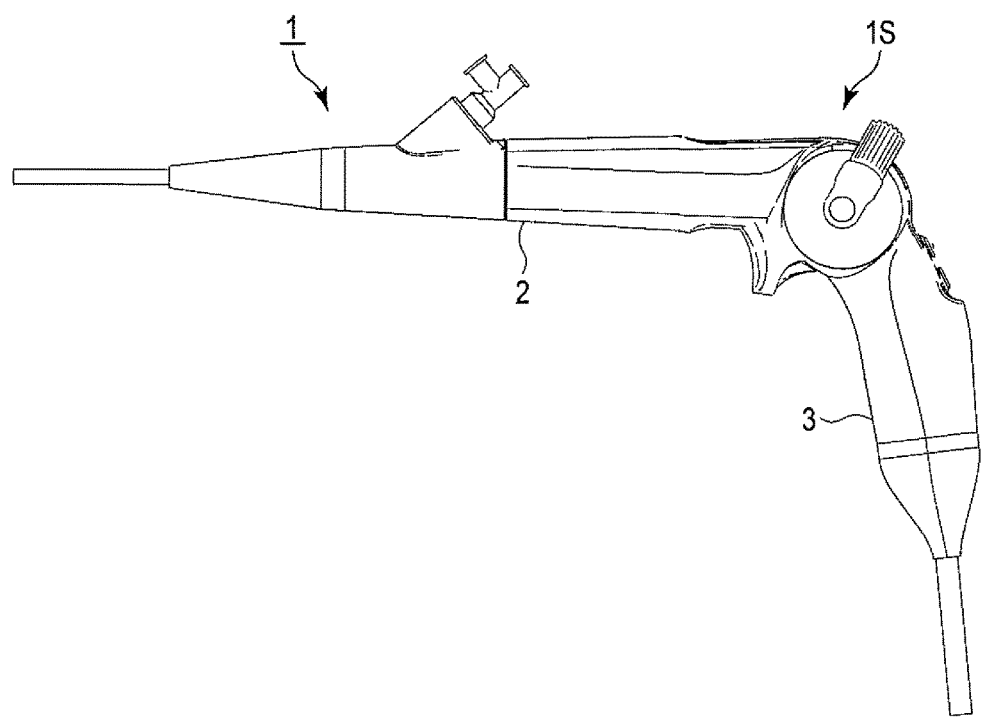
FIG. 11B is a front view of the outward appearance of the endoscope according to the embodiment.
Figure 11C:
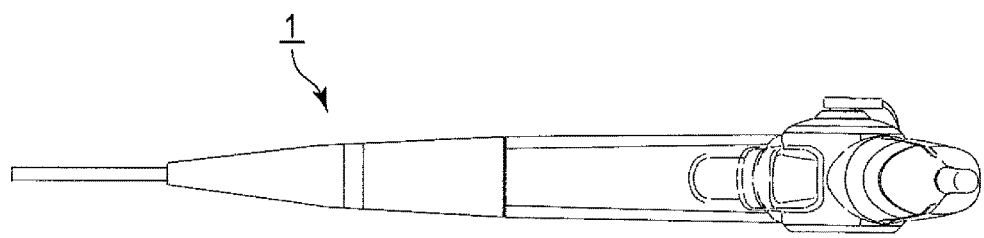
FIG. 11C is a bottom view of the outward appearance of the endoscope according to the embodiment.

FIG. 2 is a diagram showing an outward appearance of an operation unit of the endoscope apparatus according to the embodiment. FIG. 3A is a diagram showing a first structure example of a switch provided in the upper part of a rear housing section of the operation unit, and FIG. 35 is a diagram showing a second structure example of the switch. FIG. 4A is a diagram showing an outward appearance of the operation unit according to the embodiment, which is viewed obliquely from behind. FIG. 4B is a diagram showing an outward appearance of the operation unit, which is viewed obliquely from the front. FIG. 11A is a front view of an outward appearance of the endoscope according to the present embodiment, FIG. 11B is a plan view (top view) thereof, and FIG. 11C is a bottom view thereof. FIG. 12A is a rear view of the outward appearance of the endoscope, FIG. 12B is a left-side view thereof, and FIG. 12C is a right-side view thereof.

The endoscope apparatus according to the present embodiment includes an operation unit 1S, and the operation unit 1S is a gun-shaped (L-shaped) type whose insertion section 4 extends in the horizontal direction. The insertion section 4 is elongated and extends along a first longitudinal axis and its distal end is provided with a curving portion 4a. The face of the distal end of the insertion section is provided with an image pickup element for picking up an image of a subject (observation target) and an opening of a forceps port. The distal end of the insertion section can be provided with an irrigation nozzle (liquid and gas)

In the present embodiment, it is assumed that the curving portion 4a has a curving mechanism of curving only in a uniaxial direction of the up and down direction (or one-plane direction). In addition, it is natural that the curving portion may have a curving mechanism of curving in a biaxial direction corresponding to the right and left direction perpendicular to the up and down direction. Though not shown, the endoscope apparatus of the present embodiment includes a light source unit that generates illumination light with which a subject portion is irradiated, a video processor that performs predetermined image processing for the picked-up video signal, a monitor that displays a video signal as an observation image, a keyboard that is an input unit, etc. in addition to the endoscope body. When the need arises, the endoscope apparatus may include a water/air supply pump unit that supplies an irrigation liquid (e.g. saline) used for, e.g. irrigation or supplies gas and an aspiration pump unit that aspirates an irrigation liquid and gas containing an unwanted material from a body cavity.

The operation unit 1S and the light source unit are connected to each other through the universal cable 5. The universal cable 5 includes a plurality of signal lines for transmitting video signals, etc. and a gas and liquid supply path (gas and liquid supply channel) and a gas and liquid discharge path, which are formed of a tube, as well as a light guide formed of an optical fiber.

The operation unit 1S of the present embodiment is shaped like a gun (a letter "L") and includes a front section 2 (first grasping section) extending in the horizontal direction and a rear housing section 3 (second grasping section) extending downward. The front section 2 and the rear housing section 3 are formed integrally as one unit. In the following descriptions, the front of the rear housing section 3 is a side which faces the front section 2 and is caught by an operator's finger when the operator grasps the operation unit, and the rear thereof is a side with which an operator's palm is put into contact when the operator grasps the operation unit. The insertion section 4 has a distal end and a proximal end when viewed from the insertion direction. The distal end is provided with the curving portion 4a and the proximal end is connected to the operation unit 1S. In the conduit of the insertion section, the signal (video signals, sensor signals, etc.) lines, light-guiding path, gas and liquid supply and discharge paths, and forceps port are placed. Obviously, neither the supply path nor the discharge path is essential.

Furthermore, the rear end bottom of the front section 2 is connected to the top end of the rear housing section 3 and they are formed integrally as one unit. A curving operation lever 7 is rotatably supported on the rear side of the front section 2. In the present embodiment, the rear housing section 3 extends at minor angle α that is formed between the central axis (first longitudinal axis) of the front section 2 and the central axis (second longitudinal axis) of the rear housing section 3, or an obtuse angle, such as a rear grip angle of 105°. This rear grip angle can be modified as appropriate to conform to a usage pattern. It is assumed here that an operator sits and grasps the operation unit 1S in front of the body of the operator. The rear grip angle is set such that the operator easily operates the curving operation lever 7 while he or she keeps his or her wrist and arm in a natural state (or the wrist is not bent).

The rear housing section 3 has an elliptical section and includes, as its outside shape, an S curve portion SC1 that is curved like letter "S" along the fingers with which an operator grasps the operation unit and an S curve portion SC2 that is also curved like letter "S" with which an operator's palm is put into intimate contact. Moreover, the rear housing section 3 is formed such that the rear portion becomes lower by one step than the front portion on both sides, and a step 14 is provided to connect the rear and front portions smoothly. This step is provided to catch the fingers easily and prevent the hand from shifting and rotating when an operator grasps the operation unit.

The rear housing section 3 has a bottom end 6 from which the universal cable 5 extends. The bottom end 6 is tapered smoothly from the bottom of the rear housing section 3 without any step. The bottom end 6 serves to prevent the universal cable 5 from being folded and also serves as part of a grip portion. Furthermore, the universal cable 5 extending from the bottom end 6 is provided to incline toward the front at several angles (e.g. clearance angle α of 5°) with respect to the central axis (second longitudinal axis) of the rear housing section 3. If this clearance angle is formed, even though an operator twists the rear housing section 3 and the universal cable 5, the universal cable 5 is separated from the body of the operator, especially the chest, abdomen and arms and is hard to be hit thereon. It is thus considered that the universal cable 5 does not prevent the operator's procedure.

Furthermore, a recess 13 whose inner surface is roundish as shown in. FIG. 3A is formed in the rear upper portion of the rear housing 3. In the recess, switches 11 and 12 are arranged to perform a driving operation such as water supply and aspiration by a depression operation. The switches 11 and 12 of the present embodiment are disk-shaped button switches that are turned on by depression and provided watertightly. Only one of the switches (switch 11 here) has on its central surface a small projection capable of identifying the switch when an operator touches it. When the operator grasps the rear housing section 3, it is assumed that the operator's thenar is brought into contact with the surface of the housing section and the switches 11 and 12 are depressed by the pressure of the thenar to cause an erroneous operation. The recess 13 is therefore formed to such a depth that the pressure is hard to apply by the thenar.

Figure 3B:
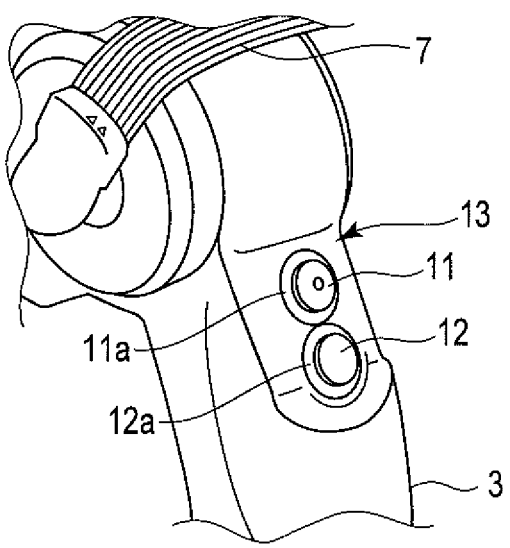
FIG. 3B is a diagram showing a second structure example of the switch.

Furthermore, as shown in FIG. 3B, a recess 13 is formed in the rear upper portion of the rear housing section 3 such that it becomes lower by one step, and the recess 13 is formed to have a curved surface as described above. Ring sections 11a and 12a are provided around the switches 11 and 12, respectively. Since these ring sections 11a and 12a are provided, the operation unit is operated if an operator depresses the switches themselves with his or her fingertips. Therefore, even though the operator grasps the operation unit and the pressure of the operator's thenar is applied, the pressure is applied to the ring sections 11a and 12a, and the switches are not depressed, with the result that no erroneous operation is performed.

According to the present embodiment, since the recess 13 is formed, the periphery of the switches 11 and 12 becomes lower than the surface of the rear housing section 3 and even though the pressure of an operator's palm is applied when the operator grasps the operation unit, the switch 11 or 12 is not depressed to prevent an erroneous operation. Since, furthermore, the recess 13 has a curved surface, even though an operator's fingertips are slightly shifted from the switches when the operator operates the switches, the fingertips are pushed and slid into the center of the recess. The switches can thus be depressed with reliability. Furthermore, since the recess 13 is formed to have a curved surface, dust is hard to collect in the recess and the recess is easy to wash.

The curving operation lever 7 of the present embodiment is an L-shaped cantilevered support including a rotation support portion 7a and an operation portion 7b. The rotation support portion 7a is supported rotatably around a rotation axis 7c on one side of the housing (connecting portion). Furthermore, the surface of the operation portion 7b has a non-slip structure in which a plurality of grooves are formed in parallel. Except for the grooves, dot-like projections can be scattered or another non-slip member can be adhered.

The curving operation lever 7 is set at the initial position 0° corresponding to almost half the angle (major angle) β at which the central axis (first longitudinal axis) of the front section 2 and the central axis (second longitudinal axis) of the rear housing 3 intersect. It is assumed here that the initial position 0° represents that the curving portion 4a of the insertion section 4 extends linearly. For example, the curving operation lever 7 is configured to grasp the operation unit by the thumb. The curving operation lever 7 is attached to a known drawing mechanism in the front section 2. If the curving operation lever 7 is rotated, wire (not shown) is drawn from the insertion section to curve the curving portion 4a.

Figure 7A:
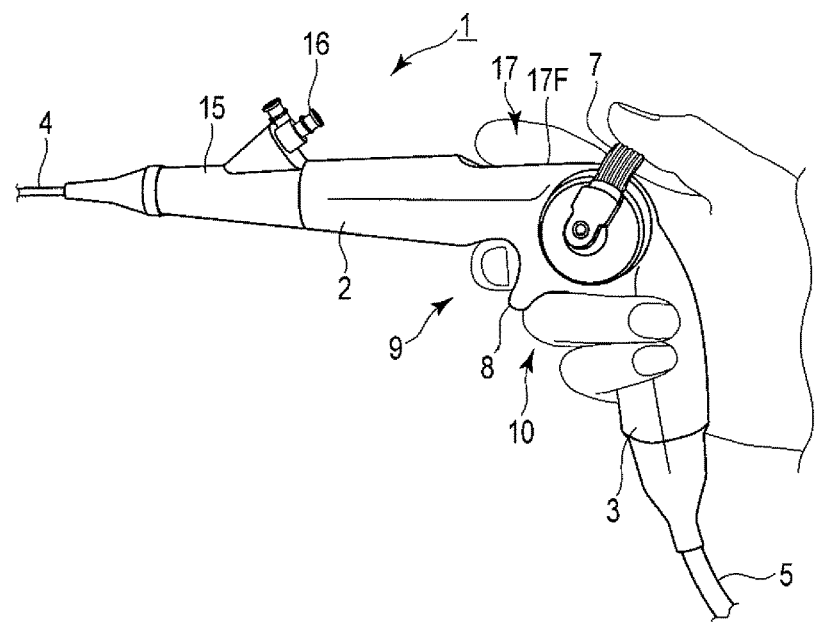
FIG. 7A is a diagram showing a second example of the operation unit grasped in the first grasping mode.

The operation unit 1S is so designed that its center of gravity is put close to the intersection of the above central axes. In the present embodiment, the center of gravity is put on a finger putting space 10 and when the operation unit 18 is grasped as shown in FIG. 7A, the center of gravity is put close to the middle finger.

In the present embodiment, to curve the curving portion 4a finely, the rotation support portion 7a is lengthened by lowering the rotation axis 7c by approximately 8 mm from the intersection of the central axis of the front portion 2 and that of the rear housing portion 3 so as to increase the rotational movement distance (circumferential length) of the operation portion 7b. Obviously, the numerical value is a design value, and the present invention is not limited to the value.

A trigger-shaped finger putting projection 8, which serves as a reference for the optimum grasping position, is formed integrally with the operation unit below the connecting portion of the rear housing section 3 and the front section 2 to separate the finger putting spaces. In contrast to the top of the projection, the trigger shape of the present embodiment has the structure in which both sides of the rear housing portion 3 and front portion 2 are formed by a concave curved surface as part of a cylindrical surface which is substantially a flat surface. The concave curved surface causes finger putting spaces 9 and 10 before and after the projection. Part of the finger putting space 9 is formed as substantially a flat surface 9F on a cylindrical front body 22.

When the operation unit 1S is grasped, if the forefinger is put in the finger putting space 9 and the middle finger is put in the finger putting space 10 as shown in FIG. 6A, the grasping positions can be optimized, the gripping force can be increased further and the grasping condition can be stabilized. In addition, the almost flat surface 9F of the finger putting space 9 is located on the lower surface of the front section. Thus, a portion of the front body 22 with which the forefinger comes into contact increases in area and even though an operator grasps the operation unit for a long time, he or she is hard to feel pain. It is therefore possible to achieve a finer observation and procedure even though an operator grasps the operation unit for a long time.

Next, the front section 2 will be described.

The front section 2 is tapered toward the insertion section 4 and its section is cylindrical or elliptic. In the present embodiment, the front section 2 has an outer circumference close to that of the rear housing section 3 in order to cause the front section 2 to serve as the first grasping section in place of the rear housing section 3 (second grasping section). The front section 2 includes a front body 22 serving as the first grasping section, a distal-end rotation section 21 that can be rotated by a rotation mechanism (shown in FIG. 9), and a tapered distal-end portion 15 having a function of preventing the insertion section 4 from being folded by fixing the proximal end of the insertion section 4.

The distal-end rotation section 21 is provided with a forceps port 16 that is an opening, and the forceps port 16 communicates with the forceps port of the insertion section 4. The distal-end rotation section 21 is fixed to the distal-end portion 15, and the insertion section 4 and forceps port 16 are formed integrally with the distal-end rotation section 21 and rotated together. In the present embodiment, it is assumed that the forceps port 16 rotates and moves to the opposite side of the distal-end rotation section 21 within a rotation range from at least 180° to 360° exclusive. If the forceps port 16 is rotated, its position can be changed to the optimum one in accordance with a grasping mode. For the following descriptions, it is assumed here that the configuration in which the forceps port 16 is placed on the upper side of the front section 2 (the side where the front section 2 and the rear housing section are not connected) as shown in FIG. 2 is a first configuration, the position of the forceps port 16 is a reference placement position, and the configuration in which the forceps port 16 is placed on the lower side of the front section 2 (the side where the front section 2 and the rear housing section are connected) is a second configuration.

The front body 22 has such a length that it is grasped by a hand and also has a front grip length to prevent a problem from being caused in an operation of inserting and ejecting forceps into and from the forceps port 16 when the front body 22 is grasped. Moreover, a finger putting space 17 is formed on the upper surface of the front body 22. The finger putting space 17 has an almost flat surface 17F that is almost parallel to the almost flat surface 9F of the finger putting space 9 from the curving operation lever 7 to a finger (e.g. a forefinger) when the rear housing section 3 is grasped.

Like the rear housing section 3, the front body 22 is so formed that the upper surface becomes lower by one stage than the lower surface and a step 18 is provided to connect these surfaces smoothly. The step 18 makes a finger putting condition comfortable and makes it difficult to cause an undesired finger shift or rotation when the front body 22 is grasped.

Next, an example of the rotation mechanism conceptually shown in FIG. 10 will be described. FIG. 10A shows an example of the structure of bonding surface A of the front body 22 shown in FIG. 2, and FIG. 10B is an example of the structure of bonding surface B of the distal-end rotation section 21 shown in FIG. 2.

The distal-end rotation section 21 is rotatably coupled to the front body 22 by fitting and coupling a fixing shaft 34 and a rotating shaft 35. For example, a bearing and an O-ring are interposed between the fixing and rotating shafts 34 and 35 to allow the distal-end rotation section 21 to rotate. Though not shown, the outer surface of the contact of the distal-end rotation section 21 and the front body 22 is made watertight by a waterproof member (not shown).

The contact surface A of the front body 22 is provided with arc-shaped light emitting windows 31a and 31b which split illumination light guided from the optical fiber of the universal cable 5 into two light beams and then emit the light beams. In this example, the rotation range (angle) is set at 180°. If the positions of the light emitting windows 31a and 31b are changed, the rotation range of the distal-end rotation section 21 can be changed. Furthermore, the distal-end rotation section 21 that is bonded to the front body 22 is provided with an illumination light incident window 32 which coincides with the light emitting window 31a. When the front body 22 and the distal-end rotation section 21 are bonded, they are opposed close to a pole so as to prevent light from leaking out, like an optical connector. The surfaces of the light incident window 32 and light emitting windows 31a and 31b are slightly retreated from the contact surface. Even though the contact surface is put into contact with the surfaces of the windows by the rotation, the contact surface does not rub against the surfaces of the window. If the operation unit 1S is configured as shown in FIG. 2, the forceps port 16 shown in FIG. 10B is located in the upper portion, the light incident window 32 is opposed to the light emitting window 31a, and illumination light is incident upon the light incident window 32 through the light emitting window 31a and then emitted from an illumination window (not shown) provided at the distal end of the insertion section 4. If the operation unit 1S is configured as shown in FIG. 5, which will be described later, the forceps port 16 (indicated by dotted lines) is rotated downward as shown in FIG. 10B, the light incident window 32 (dotted lines) moves to face the light emitting window 31b, and illumination light is incident upon the light incident window 32 through the light emitting window 31b and then emitted from the illumination window.

If, furthermore, a signal line 33 other than a fiber cable and a tube of supply and discharge paths are formed like a spiral of one winding or two windings such as a curl cord, a load applied when the distal-end rotation section 21 rotates can be reduced. To prevent the distal-end rotation section 21 from rotating undesirably during the operation, a stop mechanism is provided. In this example, a V-shaped groove 36 is formed in the distal-end rotation section 21 and a stopper unit 37 is provided at the front body 22. The stopper unit 37 is configured by a spherical stopper that is attached to an elastic member such as a spring and moves forward and backward. The stopper drops in the V-shaped groove 36 to prevent the distal-end rotation section 21 from rotating undesirably. If, furthermore, the elasticity of the elastic member is changed, the stopping force to prevent the rotation can be controlled as appropriate.

An example of switching between two angles of 0° and 180° has been described. If the angle range is from 0° to 180°, the distal-end rotation section 21 can be stopped at an arbitrary angle by removing a light-shielding section 31c of a light emitting window 31 and forming a V-shaped groove 36. Furthermore, it can be stopped at an angle of 180° or more by changing the length of the circumference of the light emitting window 31.

Next, the grasping mode of the operation unit 1S will be described with reference to FIGS. 6A through 9B. In the following descriptions, a mode in which the operation unit 1S is grasped such that the insertion section extends in the almost horizontal direction which is substantially the same as the direction in which the insertion section is inserted into a patient is referred to as a first grasping mode, and a mode in which the operation unit 1S is grasped such that the insertion section extends in the vertical direction is referred to as a second grasping mode (a grasping mode of the conventional operation unit).

FIGS. 6A, 6B, 7A, 7B and 8 show an example in which the operation unit 1S is grasped in the first grasping mode. FIGS. 9A and 9B show an example in which the operation unit 1S is grasped in the second grasping mode.

In a first example of the first grasping mode shown in FIGS. 6A and 6B, an operator puts the forefinger on the finger putting space 9 and the middle finger on the finger putting space 10 to catch the finger putting projection 8 and thus grasp the rear housing section 3. In this grasping mode, the weight of the operation unit 1S is applied to the middle finger and the rear housing section 3 is grasped with the wrist in a natural state. Thus, the grasping state is stabilized, which makes it easy to perform a lever operation and a switch operation by the thumb and reduces a burden on the operator. The insertion section 4 extends in the almost horizontal direction which is substantially the same as the direction in which the insertion section 4 is inserted into a patient, and is not bent. If, therefore, the operator twists the wrist, the insertion section 4 can be rotated, and the curving direction of the curving portion 4a can easily be changed. Unlike the conventional insertion section, the insertion section 4 is not bent; thus, a loss of the driving force transmission mechanism (e.g. wire and a pulley) in the insertion section can be reduced, and intrinsic torque follow-up and curving performance of the insertion section can be improved. In the first grasping mode, the operator can make an observation and perform a procedure in his or her seat and thus operator fatigue can be reduced.

Figure 7B:
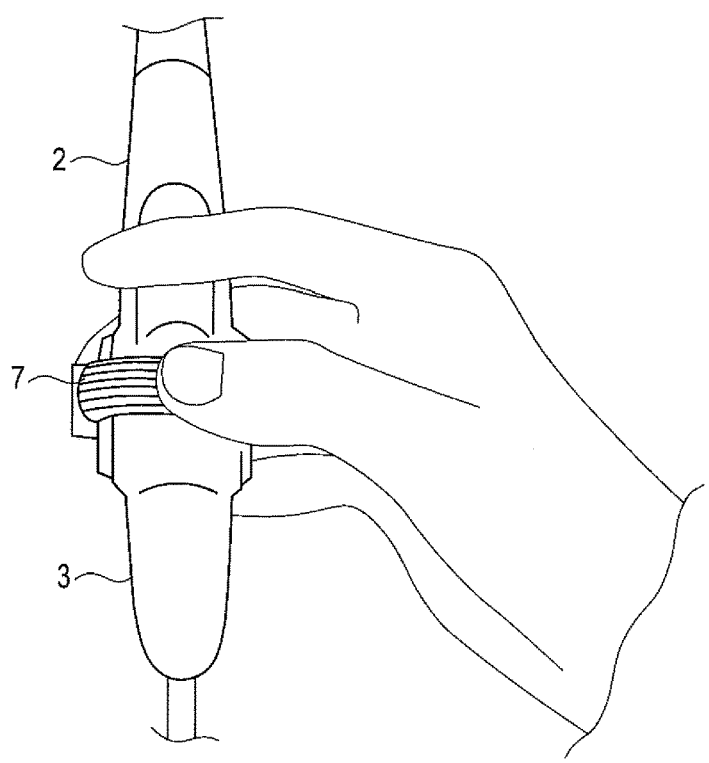
FIG. 7B is a diagram showing the second example of the operation unit grasped in the first grasping mode.

In a second example of the first grasping mode shown in FIGS. 7A and 7B, an operator puts the middle finger on the finger putting space 9 and the third finger on the finger putting space 10 to catch the finger putting projection 8 and thus grasp the rear housing section 3. The operator also puts the forefinger on the finger putting space 17 on the flat top surface of the front body 22 to grasp the rear housing section 3. According to this mode, in addition to the foregoing advantage of the first grasping mode shown in FIG. 6A, the following advantage can be brought about. Since the forefinger is put on the front body 22, the central axis of the front section 2, or the central axis of the proximal end of the insertion section 4 becomes closer to the central axis of the arm (the central axis of the rotation of the wrist) of the operator. Thus, the wrist twist operation for rotating the insertion section 4 is transmitted more minutely to allow a finer observation and procedure. Moreover, an interval between the curving operation lever 7 and the thumb is narrowed and thus even an operator whose hands are small can operate the curving operation lever 7 comfortably. Further, the curving operation lever 7 can be operated in the lateral direction and thus the fatigue of the thumb can be reduced. Furthermore, the finger putting spaces 9 and 17 are formed in the front body 22 and have almost flat surfaces 9F and 17F, respectively. Thus, the area of a portion on which the forefinger and the middle finger are hit increases, and the operator is hard to feel pain even though the operator uses the curving operation lever 7 for a long time.

Figure 8:
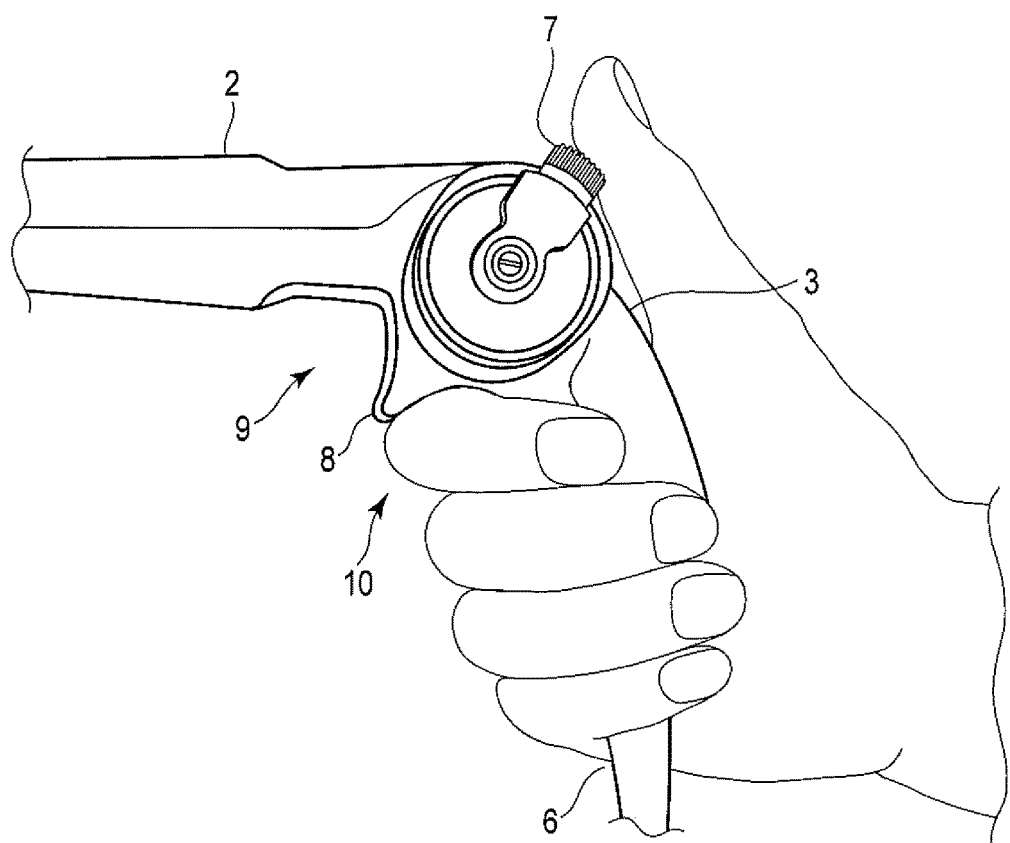
FIG. 8 is a diagram showing a third example of the operation unit grasped in the first grasping mode.
Figure 9A:
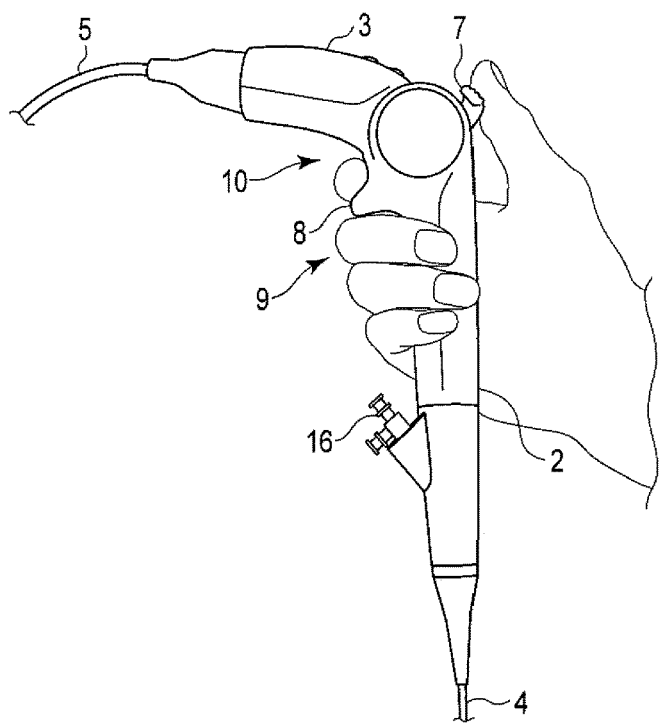
FIG. 9A is a diagram showing a first example of the operation unit grasped in a second grasping mode.
Figure 9B:
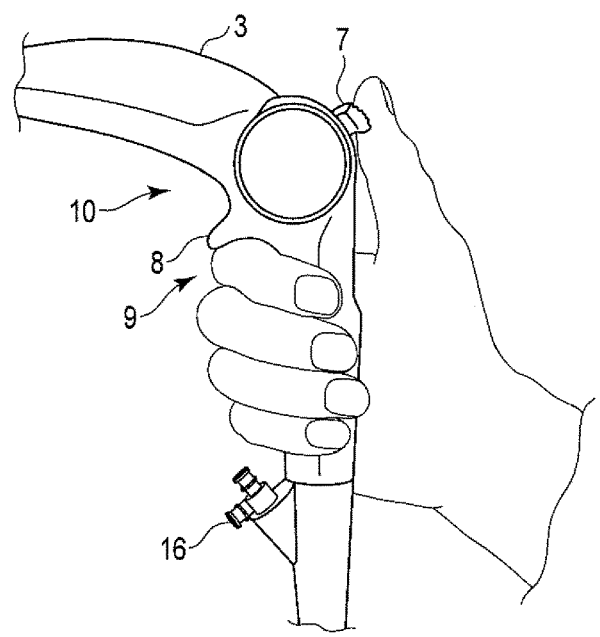
FIG. 9B is a diagram showing a second example of the operation unit grasped in the second grasping mode.

In the first grasping mode shown in FIG. 8, an operator grasps the rear housing section 3 excluding the finger putting space 10 but including the finger putting space 10. This grasping mode increases a distance between the curving operation lever 7 and the thumb and allows even an operator whose hands are large to grasp the lever comfortably.

Next, the conventional grasping mode will be described. FIG. 9A is a diagram showing a first example in which the operation unit is grasped in the second grasping mode and FIG. 9B is a diagram showing a second example in which the operation unit is grasped in the second grasping mode.

In the second grasping mode shown in FIG. 9A, the distal-end rotation section 21 shown in FIG. 2 is rotated 180° to move the forceps port 16 from the upper part of the front section 2 to the lower part thereof. With this rotation, the forceps port 16 is placed on the rear housing section 3 as shown in FIG. 5.

In the second grasping mode, an operator puts the hand from the front section 2, puts the forefinger and middle finger on the finger putting spaces 10 and 9, respectively and then catches the finger putting projection 8. This grasping mode narrows a distance between the curving operation lever 7 and the thumb and allows the operator to grasp the lever comfortably.

In the second grasping mode shown in FIG. 9B, an operator puts the forefinger on the finger putting space 9 and grasps the front section 2.

In these second grasping modes, an operator can grasp an operation unit of a conventional type (the insertion section extends from the lower part) to make an observation and perform a procedure through the same operation as that of the conventional operation unit. Since the front section 2 is thinned more than a grip portion of the conventional operation unit, even an operator whose hands are small can easily grasp the front section. Since, furthermore, the front section 2 has a smooth step 18, the step 18 makes a finger putting condition comfortable and makes it difficult to cause an undesired finger shift or rotation when the front section 2 is grasped.

As has been described above, the operation unit of the endoscope of the present embodiment is shaped like "L" by the rear housing section 3 from which the universal cable extends and the front section 2 from which the insertion section extends.

The operation unit allows two different grasping modes to be achieved only by rotating the forceps port to change the position thereof. In the first grasping mode in which the rear housing section 3 is grasped, the insertion section extends in the horizontal direction that is substantially the same as a direction in which the insertion section is inserted into a patient. In the second grasping mode in which the front section 2 is grasped, the insertion section extends downward.

As for the operation unit 1S of the present embodiment, when the distal-end rotation section 21 is not rotated, the operation direction of the curving operation lever 7 and the curving direction of the curving portion 4a are opposite to each other in the first and second grasping modes. In other words, when an operator shifts the operation unit 1S from one hand to the other, he or she rotates the operation unit 1S 180 degrees and grasps it and thus the operation direction of the curving operation lever 7 and the curving direction of the curving portion 4a will be changed to each other. If, however, the distal-end rotation section is rotated 180 degrees further in addition to a change of the grasping mode, the operation direction of the curving operation lever 7 and the curving direction of the curving portion 4a will be the same.

In the first grasping mode, therefore, an operator can grasp the operation unit stably with his or her wrist in a natural state and easily operate the lever and switches, thus reducing a burden on the operator. Since the insertion section 4 extends in the horizontal direction that is substantially the same as a direction in which it is inserted into a patient and is not bent, the operator can rotate the insertion section 4 by twisting the wrist and easily change the curving direction of the curving portion 4a. Since, furthermore, the insertion section 4 is not bent, a loss of the driving force transmission mechanism in the insertion section is reduced, and the intrinsic torque follow-up and curving performance of the insertion section can be improved.

In the first grasping mode, an operator can make an observation and perform a procedure in his or her seat and thus operator fatigue can be reduced. In the operation unit 1S of the present embodiment, the switches 11 and 23 are placed in the recess 13 that is lower than the surface of the rear housing section 3. Thus, even though the pressure of the operator's palm is applied when the operator grasps the operation unit, neither of the switches is depressed to prevent an erroneous operation. In the second grasping mode, the insertion section extends downward, and the operation unit can be grasped in a mode to which an operator has conventionally got used and the feeling of operator's anxiety about the operation can be reduced.

According to the present invention, there can be provided an endoscope including an operation unit which can be grasped in a plurality of modes as desired by an operator and which can be operated comfortably irrespective of an operator's grasping posture.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

The invention claimed is:

1. An endoscope comprising:
    an elongated insertion section including a curving portion at a distal end thereof, the curving portion being adapted to curve in a uniaxial direction and comprising an operating instrument port at a distal end thereof, the insertion section extending along a first longitudinal axis orthogonal to the uniaxial direction;
    a first grasping section provided at a proximal end of the insertion section;
    a second grasping section connected to a proximal end of the first grasping section, the second grasping section extending along a second longitudinal axis that intersects with the first longitudinal axis so that the first grasping section and the second grasping section are positioned at a predetermined obtuse angle with respect to each other, wherein in a plane the obtuse angle is a minor angle which together with a major angle formed between the first grasping section and the second grasping section constitutes 360°;
    a curving operation lever provided between the first grasping section and the second grasping section, the curving operation lever comprising an operation portion that projects from the first grasping section and the second grasping section on a side of the major angle and having an initial position at which the operation portion divides the major angle substantially in half, the curving operation lever adapted to cause the curving portion to curve when the curving operation lever is manipulated; and
    a distal-end rotation section provided at the proximal end of the insertion section and at a distal end of the first grasping section and comprising an opening into which an operating instrument is inserted, the distal-end rotation section being adapted to rotate about the first longitudinal axis together with the opening and the insertion section and with respect to the first grasping section so that the endoscope transitions between (i) a first mode in which the opening projects from the distal-end rotation section in a direction facing a same side of the endoscope as the major angle, and (ii) a second mode in which the opening projects from the distal-end rotation section in a direction facing a same side of the endoscope as the obtuse angle.

2. The endoscope according to claim 1, wherein when the endoscope is grasped in the first mode, the second grasping section is grasped and the insertion section extends in a horizontal direction that is substantially the same as a direction in which the insertion section is inserted into a subject, and when the endoscope is grasped in the second mode, the first grasping section is grasped and the insertion section extends downward.

3. The endoscope according to claim 1, further comprising:
    a projection having a top with two sides, each of the sides of the top being formed by a concave curved surface formed in a respective cylindrical surface of the first grasping section or the second grasping section, wherein the projection projects from a connecting portion between the first grasping section and the second grasping section in a direction within the obtuse angle.

4. The endoscope according to claim 2, wherein the first grasping section includes a curved circumferential surface and a pair of substantially flat portions which are indented into the curved circumferential surface and opposed to each other with regard to the first longitudinal axis, wherein one of the substantially flat portions extends proximally into a concave curved surface.

5. The endoscope according to claim 2, wherein the second grasping section includes a recess formed to such a depth that pressure of a palm is not applied to the recess when the second grasping section is grasped.

6. The endoscope according to claim 2, wherein in the first mode, the distal-end rotation section and the first grasping section are placed such that a first plane formed by one axis in the uniaxial direction and the first longitudinal axis and a second plane formed by rotation of the curving operation lever are substantially parallel to each other.

7. The endoscope according to claim 1, wherein:
the first grasping section comprises a pair of light emitting windows,
the distal-end rotation section comprises an illumination light incident window, and
in the first mode, the illumination light incident window is opposed to a first of the light emitting windows, and in the second mode, the illumination light incident window is opposed to a second of the light emitting windows.

\* \* \* \* \*